United States Patent [19]

Greenberg

[11] 4,134,977

[45] Jan. 16, 1979

[54] METHOD FOR PRODUCING INSECT-COMBATTING DEVICE

[75] Inventor: Jack Greenberg, Richmond, Va.

[73] Assignee: A. H. Robins Company, Incorporated, Richmond, Va.

[21] Appl. No.: 836,718

[22] Filed: Sep. 26, 1977

Related U.S. Application Data

[63] Continuation-in-part of Ser. No. 812,334, Jul. 1, 1977, abandoned, which is a continuation-in-part of Ser. No. 740,671, Nov. 10, 1976, abandoned, which is a continuation-in-part of Ser. No. 627,671, Oct. 31, 1975, Pat. No. 3,996,348, which is a continuation-in-part of Ser. No. 417,704, Nov. 20, 1973, Pat. No. 3,918,407.

[51] Int. Cl.² .................... A61K 31/74; A01N 9/36
[52] U.S. Cl. ..................................... 424/78; 424/225
[58] Field of Search .......................... 424/78, 219, 225

[56] References Cited

U.S. PATENT DOCUMENTS

| | | | |
|---|---|---|---|
| 2,903,478 | 9/1959 | Lambrech | 424/300 |
| 2,960,430 | 11/1960 | Jones et al. | 424/300 |
| 3,318,769 | 5/1967 | Folckemer et al. | 424/219 |
| 3,344,021 | 9/1967 | Menn et al. | 424/78 |
| 3,398,225 | 8/1968 | Bellin | 424/219 |
| 3,608,062 | 12/1968 | Alfres et al. | 424/78 |
| 3,630,446 | 12/1968 | Roth et al. | 424/219 |
| 3,852,416 | 12/1974 | Grubb et al. | 424/300 |
| 3,966,902 | 6/1976 | Chromecek | 424/224 |

FOREIGN PATENT DOCUMENTS 91898   8/1972   German Democratic Rep.

Primary Examiner—Albert T. Meyers
Assistant Examiner—D. W. Robinson

[57] ABSTRACT

An improved method for the formation of naled-containing synthetic resin shaped bodies is disclosed. A mixture of a synthetic resin, naled, and a surface porosity control component is extruded in the presence of an acid-resistant material (e.g., nickel or nickel alloys or the like). Other insecticides (e.g., carbamates) may also be included in the naled-containing mixture, if desired. The resulting extrudates are useful as pet collars or the like and are formed without substantial degradation of the naled as has been found to occur in attempts to extrude in the presence of carbon steel.

13 Claims, No Drawings

METHOD FOR PRODUCING INSECT-COMBATTING DEVICE

CROSS-REFERENCE TO RELATED APPLICATIONS

This application is a continuation-in-part application of U.S. Patent Application Ser. No. 812,334, filed July 1, 1977, and now abandoned, which application in turn is a continuation in part of application of U.S. Patent Application Ser. No. 740,671, filed Nov. 10, 1976, and now abandoned, which application in turn is a continuation-in-part application of U.S. Patent Application Ser. No. 627,671, filed Oct. 31, 1975, now U.S. Pat. No. 3,996,348, which application in turn is a continuation-in-part application of U.S. Patent Application Ser. No. 417,704, filed Nov. 20, 1973, now U.S. Pat. No. 3,918,407.

BACKGROUND OF THE INVENTION

This invention relates to a process for the preparation of an insecticide-containing device such as a pet collar for the control of fleas or ticks on warm blooded animals or a pest strip or the like for the control of common houseflies (*Musca domestica*), fruit flies (*Drosphila melanogaster*), mosquitoes (*Culex pipiens*) or the like. In particular, this invention relates to a novel process for the manufacture of a shaped body comprised of a synthetic resin having dispersed therein the insecticide 1,2-dibromo-2,2-dichloroethyl dimethyl phosphate, commonly known as naled, alone or in combination with one or more other insecticides.

Heretofore, insect-combatting devices, such as pet collars, pest strips and the like, comprised of a PVC resin having a dispersion of the insecticide dimethyl 2,2-di-chlorovinyl phosphate, commonly known as DDVP or by its trademark Vapona, have been widely used for the purpose of controlling fleas and flying insects such as houseflies, mosquitoes and the like in the vicinity of the device. However, DDVP has been reported to have an objectionable depressing effect on the plasma and red cell cholinesterase at least in animals which effect is particularly acute at high concentrations which are produced during the first few days after a pest strip has first been exposed to the atmosphere. This is believed due to the fact that the liberation rate of DDVP from presently available DDVP-containing pest strips is not uniform but rather is higher during the first few days after activation, i.e., removal of the pest strip from the packing and exposing it to the atmosphere. There are also indications that DDVP may be harmful to humans. Pest strips containing DDVP have been banned in Holland. Moreover, the aforementioned initial high liberation rate represents an unduly rapid loss of insecticide and creates an upper limit on the period that DDVP is liberated at a rate sufficient to effectively control pests. DDVP also has been found to possess a high degree of residual toxicity in the area of the device, apparently from adsorption of the DDVP vapors in walls, floors, ceilings, curtains, rugs and the like. Even after a DDVP-containing device is removed from a room environment, residual DDVP vapors can often be detected for several days thereafter.

It has also been suggested to utilize other insecticides such as naled (1,2-dibromo-2,2-dichloroethyl dimethyl phosphate) in an insert-combatting device. The preparation of naled is described in U.S. Pat. No. 2,971,882 to Osmonson et al. PVC resin-naled combinations have been proposed for use as an insecticide of a general nature in French Pat. No. 1,568,198, issued Apr. 14, 1969, and in U.S. patent application Ser. No. 85,445, filed Jan. 30, 1961 (abandoned, but accessible to the public), and corresponding British Pat. No. 955,350. Netherlands published application No. 6,610,279 discloses fly strips composed of PVC-naled as well as PVC-DDVP combinations which are stated to have such high insecticide release rates as to require an outer laminate layer to retard the insecticide release. U.S. Pat. No. 3,344,021 discloses PVC-naled combinations for use as an anthelmintic composition.

A number of problems have been encountered in providing a commercially satisfactory PVC resin-naled combination for use in an insect-combatting device. First, there must be a sufficient amount of naled released to provide effective control of the insects in the vicinity of the device. Contrary to statements in the prior art disclosures, it has been found that release rates for naled are very much less than the release rates for DDVP. Naled has a low vapor pressure of about $2 \times 10^{-4}$ mm. Hg. at 20° C. as compared to that for DDVP of $1.2 \times 10^{-2}$ to be thus only about 1.7% of the vapor pressure of DDVP.

It has further been found that the inclusion of an insecticide such as naled in a synthetic resin matrix in amounts sufficient to control insects for a commercially acceptable time leads to exudation of liquid insecticide (or "spew") on the surface of the device. These liquid droplets pose serious environmental and aesthetic problems as well as significantly decreasing the effective life of the device.

Parent application Ser. No. 627,671, filed Oct. 31, 1975, now U.S. Pat. No. 3,996,348, discloses and claims an improved insect-combatting device for use against houseflies, gnats, mosquitoes and the like of a shaped solid body having a porous surface capable of gradually and continually releasing naled insecticide in an amount sufficient to provide an insecticidally active concentration of said naled over a prolonged period of time, said device comprising a synthetic resinous matrix material, from about 15 to about 35 weight percent of naled and a minor amount effective to retard spewing of the insecticide of finely divided silica and at least one $C_{14}$ to $C_{20}$ saturated aliphatic carboxylic acid or a salt or ester thereof. The device is formed from a mixture of the synthetic resin, naled, finely divided silica particles, $C_{14}$ to $C_{20}$ aliphatic saturated carboxylic acid or salt or ester thereof and a surface porosity control component that is non-reactive in the mixture and has a boiling point at or below the curing temperature to produce surface openings in communication with pores in said body by vaporization of said porosity control component to provide for release of naled gas at a rate effective to control insects in the vicinity of said body, but insufficient to form as spew on the body.

Parent application Ser. No. 417,704, now U.S. Pat. No. 3,918,407 discloses and claims an improved flea control collar for a warm blooded animal comprising a strip of flexible synthetic resin material containing between about 5 and 25 wt. percent naled and having a width, thickness and length sufficient to encircle the neck of the animal with clamping means at one end of the collars for engaging a spaced collar portion to prevent loss of the collar from the neck of the wearing animal; said strip being formed from a dispersion of a synthetic resin, naled and a surface porosity control component that is non-reactive in the dispersion and has a boiling point at or below the curing temperature of said resin, said dispersion being heated to its curing temperature to produce surface openings in communication with pores in said strip by vaporization of said porosity control component to provide for release of naled gas at a rate effective to control fleas on said animal throughout a period of at least about 90 days, but insufficient to form as droplets on the strip or to be toxic to said animal.

As disclosed in these parent applications, the insect-combatting device may be formed by a variety of techniques. It is further disclosed that a further unexpected problem found with a PVC-naled composition was the tendency of the resin to decompose during the shaping process. For example, unsatisfactory results were obtained in early tests where naled was substituted for DDVP in PVC combinations employed in extrusion apparatus used for making PVC-DDVP pet collars known in the art. Burning and charring of the extrudate were found to occur during curing of the collars, and the finished collar underwent an unexplainable reduction in the naled concentration as compared with the naled concentration in the original mixture.

OBJECTS AND SUMMARY OF THE INVENTION

It is an object of this invention to provide a method of forming an insect-combatting device which alleviates or avoids the problems of the prior art.

A further object of this invention is to provide a relatively fast and inexpensive method for the production of an insect-combatting device which may contain a relatively high loading of insecticide without objectionable liquid insecticide droplet formation on the surface of the device.

It is also an object of this invention to provide a method for the formation of an insect-combatting device which minimizes the degradation of the insecticide during the forming process.

It is also an object of this invention to provide a method for the formation of an insecticide-containing device which device can have a variety of sizes, shapes and uses.

In one aspect, the present invention provides a process for forming a shaped solid body having a porous surface capable of gradually and continually releasing naled insecticide in an amount sufficient to provide an insecticidally active concentration of said naled over a prolonged period of time, comprising extruding a mixture of a synthetic resinous matrix material, from about 5 to about 35 weight percent of naled and a surface porosity control component that is non-reactive in the mixture and has a boiling point at or below the curing temperature to produce surface openings in communication with pores in said body by vaporization of said porosity control component to provide for release of naled gas at a rate effective to control insects in the vicinity of said body, but insufficient to form as spew on the body, the said extrusion being conducted in the presence of acid-resistant material.

As noted above, the extrusion of PVC-naled compositions in extrusion apparatus used for making PVC-DDVP pet collars known in the art results in burning and charring of the extrudate and degradation of the naled contained therein. It has been found that in the presence of heat and moisture, naled becomes acidic and extremely corrosive, especially to carbon steel which is the standard material for most parts of polymer extruders. In addition, under these conditions, naled can initiate autocatalytic degradation of PVC resin. However, the extrusion of naled-containing compositions as disclosed herein in an extrusion apparatus having all of its surfaces in contact with the naled-containing composition formed of an acid-resistant material results in a uniform, highly satisfactory extruded product with minimal indications of any burning, charring or naled degradation. The process of the present application is also useful for the extrusion of mixtures containing not only naled but also other insecticides to obtain an extruded product which is uniform, reproducable and relatively constant in naled content.

The successful extrusion of naled-containing compositions offers a number of advantages as compared to other types of polymer-forming techniques, for example, casting of a plastisol dispersion. Extrusion is relatively fast and is adapted to be used with both dry and liquid (plastisol) blends. Rapidity of formation is advantageous not only because of the greater yield of acceptable product in a particular unit of time but also because the longer a naled-containing composition is maintained at an elevated temperature, the greater the liklihood that some of the naled will degrade. In addition, extrusion may be used to produce a variety of sizes and shapes which are unsuitable for production by casting. A number of other advantages of extrusion will be apparent to those skilled in the art.

DESCRIPTION OF THE PREFERRED EMBODIMENTS

The components making up a satisfactory insecticide-containing insect-combatting device include a synthetic resin that is compatible with the relatively high amounts of insecticide and a strength sufficient to maintain the integrity of the shaped device throughout the period during which the insecticide is released in amounts effective to combat insects and arachnids, e.g., fleas/ticks, flies or mosquitoes. The shaped insect-combatting device includes the synthetic resin in a concentration sufficiently large to give the device physical properties such as strength, flexibility, and freedom from tackiness so as to make it suitable for use as an insect-combatting device. Generally, the shaped device contains from about 20 to about 80, preferably from about 25 to about 60, weight percent of the synthetic resin.

The various known synthetic resins which can be used in the insect-combatting device include materials such as polyethylene, polypropylene, copolymers of ethylene and propylene, nylon, cellophane, polyacrylates, such as polymers and copolymers of methylacrylate, ethylacrylate, methylmethacrylate and ethylmethacrylate; polymers of vinyl compounds, such as polystyrene, polymerized divinylbenzene; polyvinyl halogenides, such as polyvinylchloride, polyvinyacetals, such as polyvinylbutyral; polyvinylidene compounds, such as polyvinylidenechloride; polyvinylacetate; ethylvinylacetate-vinylacetate copolymers; copolymers of vinylchloride and vinylacetate; polyurethanes, polyaldehydes; and thermopolastics.

Polyvinylchloride (PVC) homopolymers and copolymers with other polymers such as polyvinyl acetate (PVA) are preferred synthetic resin materials. Suitable PVC resins are commercially available and include, for example, PVC homopolymer dispersion resin Firestone FPC-6337 ™ and FPC-9290 ™ available from Firestone Plastics Co., PVC homopolymer dispersion resin Diamond PVC-7502 ™ and PVC homopolymer extender resin Diamond PVC-7-446 ™, both available from The Diamond Shamrock Co., PVC homopolymer extender resin Borden 2605 ™ available from the Borden Co. and FLO-WEL 405 resin available from Air Products and Chemicals Co., and mixtures thereof. Other suitable, commercially available PVC resins are known in the art. Suitable PVC-PVA copolymers are also commercially available and include, for example, Geon 135 (Goodrich Corp.), PVC-74 (Diamond Alkali Co.) and XR-6338 (Exxon-Firestone). Other PVC-PVA copolymers are also known in the art.

The improved insect-combatting device of the present invention contains naled (1,2-dibromo-2,2-dichloroethyl dimethyl phosphate) insecticide in an amount sufficient to provide an insecticidally active concentration of the insecticide over a prolonged period of time, which amount can be from about 5 to about 35, preferably from 15 to about 30, weight percent insecticide.

One or more other insecticides compatible with the naled-containing composition may also be included. For example, the composition may also contain from about 2 to about 12 weight percent of a carbamate insecticide (further defined below). The carbamate insecticides which may be utilized are disclosed in U.S. Pat. No. 3,852,416. Neither insecticide adversely affects the mode of emission of the other from the resin matrix. The carbamates are emitted from the surface of the device primarily as powders and are substantially free of naled. The carbamate does not interfere with release of vaporous naled.

Carbamates useful in combination with naled in the present invention are represented by the formula:

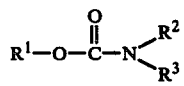

wherein;

$R^1$ is aryl, substituted aryl, heterocyclic or substituted heterocyclic groups, $R^2$ is hydrogen or lower alkyl, and $R^3$ is lower alkyl.

The term "lower alkyl" as used herein refers to an alkyl group, branched or straight chain, having a chain length of one to six carbon atoms. The term "aryl" as used herein refers to an aryl group such as phenyl or naphthyl. The term "substituted aryl" as used herein refers to a phenyl or naphthyl group substituted with one or more groups such as lower alkyl, halogen, lower alkoxy, lower alkylamino, lower dialkylamino or lower alkylthio. The term "heterocyclic" as used herein refers to an organic cyclic group having an oxygen atom, sulfur atom or one or two nitrogen atoms in the nucleus thereof and continuing up to twelve carbon atoms. The term "substituted heterocyclic" as used herein refers to a heterocyclic group substituted with one or more groups such as lower alkyl, lower alkoxy, lower alkylthio, lower alkylamino, lower dialkylamino carbamoyl or alkyl substituted carbamoyl or halogen.

Typical of the carbamates which can be used in the present invention are:

2-isopropylphenyl-N-methyl carbamate
2-isopropoxyphenyl-N-methyl carbamate
3-(1-methylbutyl)-phenyl-N-methyl carbamate
3-(1-ethylpropyl)phenyl-N-methyl carbamate
6-chloro-3,4-xylenyl-N-methyl carbamate
4-methylthio-3,5-xylenyl-N-methyl carbamate
1-naphthyl-N-methyl carbamate
1-naphthyl-N-ethyl carbamate
1-naphthyl-N-isopropyl carbamate
1-naphthyl-N-butyl carbamate
1-naphthyl-N-hexyl carbamate
1-(4-chloronaphthyl)-N-methyl carbamate
1-(5,6-dihydronaphthyl)-N-methyl carbamate
1-(5,8-dihydronaphthyl)-N-methyl carbamate
4-benzothienyl-N-methyl carbamate
2,2-dimethyl-1,3-benzodioxol-4-ol methylcarbamate
1-phenyl-3-methylpyrazol-5-yl-N,N-dimethyl carbamate
2-(N,N-dimethylcarbamyl)-3-methyl-pyrazol-5-yl-N,N-dimethyl carbamate
3,4-xylyl methylcarbamate
n-cym-5-yl methylcarbamate
o-chlorophenyl methylcarbamate The preparation of carbamates of the above formula has been previously described, for example U.S. Pat. Nos. 2,903,478 and 3,203,853.

The preferred carbamates are 2-isopropoxyphenyl-N-methyl carbamate known as propoxur (or Sendran ™) and 1-napthyl-N-methyl carbamate known as carbaryl (or sevin ™).

As noted before, the naled-containing composition fed to the extruder may be in the form of either a liquid (plastisol) dispersion or a dry powder blend with the latter being preferred. Synthetic resin, e.g., PVC, are generally available in the form of dry powders while naled, the porosity control component and resin plasticizer are generally available in liquid form. The carbamate insecticides, when utilized, are generally available in liquid form or as a powder with the carbamate being absorbed on or mixed with porous inert carrier particles, e.g., silica particles.

Plastisol formulations of these components may be prepared in a manner well-known to those skilled in the art. Generally, the liquid components are first mixed together and then the powder component (or mixture of powder components if more than one is used) is stirred with the liquid mixture gradually until a uniform plastisol dispersion results.

The dry powder blend for extrusion may be prepared by forming a uniform plastisol as above, homogenizing the plastisol into a paste in a suitable mixing device (e.g., a Hobart mixer) and drying the paste in an oven at a moderately elevated temperature, e.g., from about 140° to 175°, preferably from about 150° to about 170°, F., to form free-flowing powder which may be directly fed into the extruder. As will be apparent to those skilled in the art, the amount of naled in a particular extruded shaped body will vary depending upon the particular use for that body. That is, when the extruded shaped body is to be utilized as a collar for cats, the naled concentration is generally in the lower portion of the range (e.g., from about 5 to about 15 weight percent naled.). Similarly, the concentration of the carbamate insecticide, if utilized, will be in the lower portion of the range (e.g., from about 2 to about 3.5 weight percent) for cat collars. Dog collars generally contain a higher amount of naled (e.g., from about 15 to about 25 weight percent naled) and similarly higher amounts of carbamate, if utilized, e.g., from about 3.5 to about 12 weight percent while pest strips generally contain the highest amounts of naled (e.g., from about 20 to 35 weight percent naled).

Generally, the utilization of naled insecticide in amounts of from about 15 weight percent, more usually from about 25 to about 35 weight percent, in a synthetic resin matric leads to liquid naled droplets or "spew" formation on the surface of the insect-combatting devive. Liquid droplets of naled insecticide forming on the surface of the shaped device pose a substantial health and safety hazard as well as diminished insecticidal efficiency. The insect-combatting device of the present invention can also include a minor amount effective to retard spewing of the insecticide of finely divided silica particles and at least one $C_{14}$ to $C_{20}$ saturated aliphatic carboxylic acid or a salt or ester thereof and exhibits a substantially lessened tendency towards formation of liquid droplets of naled insecticide on its surfaces when the naled is contained in these generally higher amounts.

Although silica is known in the art, along with a number of other minerals and glasses, as a filler for various synthetic resins, it has unexpectedly been found that finely divided silica particles generally having a particle size of from about 1 to about 50, preferably from about 2 to about 10, microns, exhibit a high degree of relative efficiency in retarding insecticide spewing when utilized in sufficient amounts, which spew-retarding amounts are generally in the range of from about 10 to about 35, preferably from about 15 to about 25, weight percent of the insect-combatting device. It has been found that utilization of finely divided silica particles in an amount of less than about 10 percent by weight is generally ineffective to provide any significant retardation of the insecticide spew while utilization of finely divided silica particles in an amount above about 35 percent by weight does not result in any further reduction in spew formation.

While the addition of the finely divided silica particles exhibit a high degree of relative efficiency in retarding naled insecticide spewing, a small amount of the naled insecticide may nonetheless sometimes exude from the insecticide-containing device. It has further been found that the inclusion in the device of a minor amount of at least one $C_{14}$ to $C_{20}$ saturated aliphatic carboxylic acid or salt or ester (e.g., magnesium stearate) thereof, is effective to essentially retard any naled insecticide spewing which might otherwise occur. The $C_{14}$ to $C_{20}$ saturated aliphatic carboxylic acid, which can be a mixture of such acids, is generally utilized in an amount of from about 0.25 to about 3, preferably from about 0.5 to about 1.5, weight percent in the device. Stearic acid and palmitic acid are preferred.

While East German Pat. No. 91,898 discloses the addition of a $C_{14}$ to $C_{20}$ saturated aliphatic carboxylic acid along with a particular mixture of primary and secondary plasticizers to a polyvinyl chloride-DDVP mixture, the acid-plasticizers mixture being added to retard spewing of the DDVP, it has been found that the utilization of the $C_{14}$ to $C_{20}$ saturated aliphatic carboxylic acid alone (i.e., without the finely divided silica particles) with the resin and insecticide in the insect-combatting device of the present invention is insufficient to effectively retard spewing of the naled insecticide from the device. Similarly, the use of the finely divided silica particles alone (i.e., without the $C_{14}$ to $C_{20}$ saturated aliphatic carboxylic acid) is insufficient to effectively retard spewing of the insecticide from the device. However, the utilization of a minor amount of both the finely divided silica particles and the $C_{14}$ to $C_{20}$ saturated aliphatic carboxylic acid has been found to possess a high efficiency for insecticide spew retardation and to effectively maintain the surface of the device free of liquid droplets of the insecticide.

In the embodiments where polyvinyl resins are used, plasticizers and other additives commonly used for providing the flexibility, strength and surface characteristics desired for an insect-combatting device are well known to those skilled in this art, and no further discussion is deemed necessary here. Suitable plasticizers include esters of phosphoric acid such as tricresyl phosphate and esters of phthalic acid such as dioctyl phthalate. Other esters such as those of adipic acid, azalaic acid, maleic acid, ricinoleic acid, myristic acid, and trimellitic acid as well as complex linear polyesters, polymeric plasticizers and epoxidized soybean oils. In addition, coloring and odor control agents may also be employed to enhance consumer acceptance.

As noted above, naled has a low vapor pressure. The naled release rate from a PVC-naled device is comparatively low and may be inadequate for a commercially acceptable insect-combatting device. The use of an additive in the mixture can be very helpful in increasing the naled release rate and makes possible both effective insect control at lower initial naled concentrations and an insect-combatting device having an increased effective life.

The additive, also referred to as a surface porosity control component, is present in the final mix used in forming the device, and hence must be non-reactive with the other components of the dispersion or mix. The main function of the additive is to provide a surface porosity which preferably includes pores extending part way into the body of the device. The desired surface characteristics are obtained by the vaporization of the additive during the curing period. Hence the additive should comprise one or more compounds having a boiling point at or below the curing temperature of the resin.

Compounds which are suitable as the surface porosity control component in PVC resins which are cured at a temperature in the range of between about 260° to 400° F. include aldehydes and their lower alkyl acetals containing bromine or chlorine, generally having a boiling point of from about 170° to about 400°, preferably from about 185° to about 350°, F. The porosity control component may thus include one or more of the following which have approximate boiling point temperature as set forth:

| Name | B.P. ° F. |
| --- | --- |
| chloroacetaldehyde | 185 |
| dichloroacetaldehyde | 192 |
| chloral | 218 |
| bromoacetaldehyde | 176-221 |
| dibromoacetaldehyde | 346 |
| bromodichloroacetaldehyde | 258 |
| chlorodibromoacetaldehyde | 299 |
| bromochloroacetaldehyde | 233 |
| 2-bromopropanol | 229 |

The surface porosity control component is included in the naled-containing synthetic resin composition in an amount sufficient to produce sufficient surface porosity by its vaporization during curing of the dispersion to effectively increase the release rate of naled gas from the formed device. While the amount of the porosity control component to be used depends on the density of surface openings desired and somewhat on the particular procedure used for curing the resin, it is generally from about 0.8 to 5, preferably from about 1 to 3, weight percent of the dispersion.

The mixture is formed into a shaped body by extrusion through an extruder in which all of the surfaces which may come in contact with the naled-containing synthetic resin mixture (e.g., the feed hopper, barrel, screw, die and the like) are formed of or coated with an acid-resistant material. When the shape of the extruded body is solid, i.e., without defined internal hollows or passages, the extruder apparatus can be of any conventional type known to those skilled in the art for extruding synthetic resin mixtures. If the extruded body contains any internal hollows or passages, a cooling chamber should be provided at the exit end of the die to rapidly cool the extruded material which has a relatively low hot strength at conventional extrusion temperatures. In any case, it is critical that the extrusion be conducted in the presence of acid-resistant materials.

The acid-resistant material can be any conventional metal, metal alloy or non-metallic material which is resistant to the acidic nature of the naled material. Typically, the acid-resistant material will be aluminum, nickel or stainless steel or various alloys thereof (e.g., Xaloy, Hastelloy, Stellite or the like), nickel-plated alloys, ceramics or glass. Nickel-based alloys such as Xaloy 101 or nickel alloys containing tungsten carbide particles are especially suitable for the construction of parts such as the barrel where high abrasion resistance is required. The component parts of the extruder apparatus may be formed entirely of this material or the naled-contacting parts may be coated or plated with this material.

Extrusion may be performed under pressure and temperature conditions sufficient to produce an extruded, cured body from the synthetic resin-naled mixture. Extrusion may be carried out, for example, at a temperature of from about 200 to about 350, preferably from about 240 to about 310°, F. and a die pressure of from about 200 to about 900, preferably from about 400 to about 750, psig.

The invention is additionally illustrated in connection with the following Examples which are to be considered as illustrative of the present invention. It should be understood, however, that the invention is not limited to the specific details of the Examples.

EXAMPLE I

A mixture (in parts by weight) of 40 p.b.w. polyvinyl chloride homopolymer dispersion resin
15 p.b.w. polyvinyl chloride homopolymer blending resin
20.5 p.b.w. dioctyl phthalate (DOP)
2.5 p.b.w. epoxidized octyl tallate (EPO)
1 p.b.w. calcium-zinc stabilizer
21 p.b.w. naled (1,2-dibromo-2,dichloroethyl dimethyl phosphate)
2 p.b.w bromodichloroacetaldehyde is thoroughly triturated to form a plastisol dispersion. The plastisol dispersion is fed to a conventional type plastics extruder which has a one inch barrel with an Xaloy 800 (a commercially available nickel-based alloy containing tungsten carbide particles) liner, an aluminum die and a nickel plated screw with stellite flights such that the plastisol dispersion is fed into and extruded through the extruder in contact only with surfaces of acid-resistant material. The dispersion is extruded at a die temperature of about 265° F and a die pressure of about 600 psig to form a solid, essentially rectangular cross-section shape. The color of the extrudate is light brown and discernably lighter than similar shapes produced with similar mixtures by casting or injection molding. The lighter color of the extruded shaped indicates that there is less decomposition of the naled during extrusion than during casting or injection molding since naled at elevated temperatures has been found to decompose to form chromophors which tint an otherwise clear polyvinyl chloride resin mixture a bronze color.

The above dispersion and extender resins are as easy to work with in producing a satisfactory device as any that have been used. However, as those skilled in this art well know, a large number of other materials, as discussed above, can be used. Naled is not known to react chemically with any synthetic resin, and considerable variations in both ingredients and proportions can be successfully used.

Analysis of the extruded shape shows the naled content to be 20% by weight. Also, the surfaces of the extruded shape show a high degree of surface porosity due to the evaporation of the volatile additive from the mixture as it exits from the die face. It appears that the surface porosity of the extruded shape is higher than that generally obtained from casting or injection molding. While surface porosity is also obtained in casting or injection molding, the synthetic resin tends to fill any pores created in such processing until the resin (which is being heated) reaches its gel point. In extrusion, the resin is heated in the enclosed barrel and the volatile additives are maintained in the resin mixture until the mixture exits from the die.

The extruded shape is cut to length and a buckle attached to one end. The device is then suitable for use as pet (e.g., dog) collar.

EXAMPLE II

A mixture (in parts by weight) of 20.0 p.b.w. polyvinyl chloride homopolymer dispersion resin
11.0 p.b.w. polyvinyl chloride homopolymer blending resin
9.0 p.b.w. di-2-ethylhexylphthalate
2.5 p.b.w. epoxidized octyl tallate
1.0 p.b.w. bentone
28.0 p.b.w. naled
2.0 p.b.w. surface porosity control component (e.g., bromodichloroacetaldehyde)
25.0 p.b.w. amorphous silica particles, average particle size, 2.35 microns
1.5 p.b.w. palmitic acid is formed into a uniform plastisol dispersion by first mixing the liquid components, adding the stabilizer and then generally mixing a mixture of the other dry components. The plastisol is extruded in the extruder and under the conditions as used in Example I.

Analysis of the resulting extruded shape shows the naled content to be 26% by weight and the extrudate is suitable for use as a dog collar.

EXAMPLE III

A mixture (in parts by weight) of 36.0 p.b.w. polyvinyl chloride homopolymer dispersion resin
15.0 p.b.w. polyvinyl chloride homopolymer extender resin
19.0 p.b.w. dioctyl phthalate
3.0 p.b.w. epoxidized octyl tallate
1.0 p.b.w. calcium-zinc stabilizer
19.0 p.b.w. naled
2.0 p.b.w. bromodichloroacetaldehyde
5.0 p.b.w. propoxur (a powder of 90% 2-isopropoxyphenyl N-methyl carbamate and 10% amorphous silica)

is formed into a uniform plastisol dispersion by first mixing the liquid components, adding the stabilizer and then gradually mixing a mixture of the other dry components. The plastisol is extruded in the extruder and under the conditions as used in Example I.

Analysis of the resulting extruded shape shows the naled content to be 18% by weight and the propoxur content to be 4.5% by weight. The extrudate is suitable for use as a dog collar.

carbamate powder (propoxur) silica. The polyvinyl chloride resins, which in these Examples are dry powders, are uniformly mixed and added to the liquid mixtures. The total mixture is then homogenized into a paste in a Hobart mixer. The paste is dried into free-flowing powder particles in an oven at 160° F. The particles are then fed directly into he extruder of Example I or cooled for later use in such an extruder. The powder is extruded under the conditions of Example I.

In Examples V, VI, XI and XII, a low molecular weight homopolymer resin is added, as the blending resin, to reduce fusion temperature. In Examples VII, VIII, and IX, propylene-vinyl chloride copolymers are added to increase the melt flow of the mixture. The small amounts of silica and stearic acid are added to reduce the diffusional resistance of naled in the polyvinyl chloride matrix and as a lubricant, respectively.

Each of the extruded samples shows a porous surface and when assayed shows a very little loss in naled content (i.e., about 1% or less in each case) from the originally added. The extruded samples are suitable for use as pet collars.

| EX. NO. | POLYVINYL CHLORIDE RESIN p.b.w. DISPERSION RESIN | POLYVINYL CHLORIDE RESIN p.b.w. BLENDING RESIN | VINYL CHLORIDE PROPYLENE CO-POLYMER p.b.w. | PLASTICIZERS p.b.w. | NALED p.b.w. | PROPOXUR p.b.w. | BROMODICHLOROACETALDEHYDE SURFACE POROSITY CONTROL AGENT, p.b.w. | STABILIZER, COMPOUND, pbw | STEARIC ACID, pbw | FINELY-DIVIDED SILICA PARTICLES |
|---|---|---|---|---|---|---|---|---|---|---|
| V | 34.9 | 23.0 | — | 22 | 16.2 | — | 1.8 | Magnesium-Zinc 1.9 | 0.2 | — |
| VI | 35.0 | 22.3 | — | 22.5 | 16.2 | — | 1.8 | ", 0.5 | 0.2 | 1.5 |
| VII | 38.4 | — | 21.0 | 22.0 | 16.2 | — | 1.8 | Calcium-Zinc, 0.5 | 0.1 | — |
| VIII | 37.5 | — | 17.5 | 24.0 | 16.2 | — | 1.8 | Barium-Cadmium, 1.0 | — | 2 |
| IX | 35.9 | — | 23.0 | 20 | 17.1 | — | 1.9 | Magnesium-Zinc, 2 | 0.1 | — |
| X | 20 | 11 | — | 12.5 | 28 | — | 2 | | 1.5 | 25 |
| XI | 35.5 | 20.4 | — | 21.0* | 16 | 5.0** | 1.6 | Calcium-Zinc, 0.5 | — | — |
| XII | 42.0 | 21.0 | — | 24.0* | 8.5 | 3.0** | 1.0 | ", 0.5 | — | — |

*Includes 3.0 p.b.w. epoxidized octyl tallate stabilizer
**Includes 10 weight percent (of the total amount of propoxur) of silica particles

EXAMPLE IV

Example III is repeated using a mixture (in parts by weight) of 42.0 p.b.w. polyvinyl chloride homopolymer dispersion resin
16.0 p.b.w. polyvinyl chloride homopolymer extender resin
21.0 p.b.w. dioctyl phthalate
3.0 p.b.w. epoxidized octyl tallate
1.0 p.b.w. calcium-zinc stabilizer
12.5 p.b.w. naled
1.5 p.b.w. bromodichloroacetaldehyde
3.0 p.b.w. propoxur The plastisol is extruded as described in Example I. The extrude contains 12 weight percent naled and 2.5 weight percent propoxur.

EXAMPLES V - XII

Mixtures are made of the formulations shown in Table I. In each case, the liquid components (plasticizers, naled and surface porosity control component) are uniformly mixed with the stabilizer, stearic acid and

EXAMPLE XIII

The mixture and procedure of Example X is repeated except that 30 weight percent of a technical grade of naled (1,2-dibromo-2,2-dichloroethyl dimethyl phosphate) commercially available from the Chevron Company is used. This product is known to contain certain impurities such as bromodichloroacetaldehyde, chloral, carbon tetrachloride and various forms of phosphates. These impurities constitute about 9 weight percent of the product and in large part are sufficiently volatile as to be released during the extrusion of the mixture and hence not to interfere with the functioning of the collar.

The device formed in the manner indicated contains about 26 weight percent naled.

COMPARATIVE EXAMPLE

A mixture similar to that used in Example V with about 54 weight percent polyvinylchloride resin, 19 weight percent dioctyl phthalate, 3 weight percent epoxidized octyl tallate stabilizer, 1 weight percent of antioxidant and 23 weight percent technical grade of naled (as in Example XIII) is extruded in a conventional extruder used for making pet collars of polyvinyl chloride and DDVP (dimethyl 2,2-dichlorovinyl phosphate), which extruder is formed primarily in its mixture-contacting surfaces of plain carbon steel which is not acid-resistant. Burning and charring of the extrudate are found to occur and the extruded collar contains significantly less naled (about 18 weight percent) than originally present. In the presence of heat and moisture, the naled becomes acidic and extremely corrosive, especially to carbon steel thus resulting in naled and steel degradation. Also, the naled initiates autocatalytic degradation of the PVC resin.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a process for forming a shaped body of a mixture of from about 20 to about 80 weight percent of a polyvinyl chloride resin; from about 5 to 35 weight percent of naled; from about 0.8 to about 5 weight percent of a surface porosity control component that is non-reactive in the mixture and has a boiling point at or below the curing temperature of the polyvinyl chloride to produce surface openings in communication with pores in said body by vaporization of said porosity control component during curing to provide for release of naled gas at a rate effective to control insects in the vicinity of said body, but insufficient to form as spew on the body; and finely divided silica particles, the improvement comprising extruding said mixture in an extruder, all of the surfaces thereof which contact said mixture being formed of an acid-resistant material.

2. In the process of claim 1 wherein the mixture further includes from about 2 to about 12 weight percent of at least one carbamate insecticide having the structural formula $$R^1-O-\overset{O}{\underset{\|}{C}}-N\overset{R^2}{\underset{R^3}{\diagdown}}$$

wherein;
R$^1$ is aryl, substituted aryl, heterocyclic or substituted heterocyclic groups,
R$^2$ is hydrogen or lower alkyl, and
R$^3$ is lower alkyl.

3. In a process for forming a shaped body of a mixture of a synthetic resinous matrix material, from about 5 to 35 weight percent of naled, and a surface porosity control component that is non-reactive in the mixture and has a boiling point at or below the curing temperature of the synthetic resin to produce surface openings in communication with pores in said body by vaporization of said porosity control component during curing to provide for release of naled gas at a rate effective to control insects in the vicinity of said body, but insufficient to form as spew on the body, the improvement comprising extruding said mixture in an extruder, all of the surfaces thereof which contact said mixture being formed of an acid-resistant material.

4. The process of claim 3 wherein said mixture further includes at least one other insecticidally active material.

5. The process of claim 4 wherein said mixture further includes from about 2 to about 12 weight percent of at least one carbamate insecticide having the structural formula $$R^1-O-\overset{O}{\underset{\|}{C}}-N\overset{R^2}{\underset{R^3}{\diagdown}}$$

wherein;
R$^1$ is aryl, substituted aryl, heterocyclic or substituted heterocyclic groups,
R$^2$ is hydrogen or lower alkyl, and
R$^3$ is lower alkyl.

6. The process of claim 5 wherein said synthetic resinous matrix material is a polyvinyl chloride.

7. The process of claim 6 wherein said surface porosity control component has a boiling point of from about 170° F. up to the curing temperature of the polyvinyl chloride synthetic resinous material.

8. The process of claim 7 wherein said surface porosity control component is selected from the group consisting of chloroacetaldehyde, dichloroacetaldehyde, chloral, bromoacetaldehyde, dibromoacetaldehyde, bromal, bromodichloroacetaldehyde, chlorodibromoacetaldehyde, bromochloroacetaldehyde, 2-bromopropanol and mixtures thereof.

9. The process of claim 5 wherein said mixture contains from about 15 to 35 weight percent naled, from about 10 to about 35 weight percent of finely divided silica particles, from about 0.25 to about 3 weight percent of at least one C$_{14}$ to C$_{20}$ aliphatic saturated carboxylic acid or a salt or ester thereof and from about 0.8 to about 5 weight percent of said surface porosity control component.

10. The process of claim 5 wherein the mixture is extruded at a temperature of from about 200° to about 350° F.

11. The process of claim 10 wherein the mixture is extruded at a temperature of from about 240° to about 310° F.

12. The process of claim 3 wherein the said mixture comprises a dry powder blend prior to extrusion.

13. The process of claim 12 wherein the dry powder blend is formed by homogeneously combining the components of said mixture and then drying the homogeneous combination.